United States Patent [19]

Rautenstrauch

[11] Patent Number: 4,499,297

[45] Date of Patent: Feb. 12, 1985

[54] PROCESS FOR THE PREPARATION OF ALKYLATED CYCLOPENTENONES

[75] Inventor: Valentin Rautenstrauch, Bernex, Switzerland

[73] Assignee: Firmenich, SA, Geneva, Switzerland

[21] Appl. No.: 552,462

[22] Filed: Nov. 16, 1983

[30] Foreign Application Priority Data

Dec. 6, 1982 [CH] Switzerland .......................... 7075/82

[51] Int. Cl.³ ...................... C07C 45/48; C07C 69/145
[52] U.S. Cl. ...................................... 560/231; 560/261; 560/113; 568/356
[58] Field of Search ....................... 560/261, 231, 113; 568/356

[56] References Cited

U.S. PATENT DOCUMENTS 2,870,208  1/1959  Guex et al. ............................ 568/356
4,317,905  3/1982  Wassardo et al. .................... 560/261

FOREIGN PATENT DOCUMENTS 2513198  10/1975  Fed. Rep. of Germany ....... 560/261

OTHER PUBLICATIONS

Golden et al., J. Chem. Soc., Chem. Comm., 1981, pp. 1030-1031.
Funk et al., Synthesis, 1980, p. 118.
Naef et al., Helv. Chim. Acta., vol. 61, p. 2524 (1978).
Ho et al., Chem. Ind., 1982, pp. 371-372.
McCurry et al., J. Org. Chem., vol. 39, pp. 2317-2319 (1974).
Grieco et al., J.A.C.S., vol. 102, p. 7587 (1980).

*Primary Examiner*—James H. Reamer

*Attorney, Agent, or Firm*—Scully, Scott, Murphy & Presser

[57]  ABSTRACT

Cyclopentenones of formula

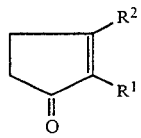

(I)

wherein each of symbols $R^1$ and $R^2$, when taken separately, represents an alkyl radical of $C_1$ to $C_6$, or a hydrogen atom, or, when taken together, they represent a polymethylene, or one of them designates a hydrogen atom and the other an alkyl radical of $C_1$ to $C_6$, are prepared starting from compounds having formula

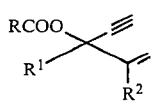

(II)

wherein R stands for a $C_1$ to $C_6$ alkyl radical or a phenyl group, via a catalytic reaction promoted by a metalloorganic compound of formula $$MeX_2(R^3CN)_2 \qquad (III)$$

wherein Me represents palladium or platinum, $R^3$ represents a $C_1$ to $C_3$ alkyl radical or a phenyl group and X defines a halogen atom.

12 Claims, No Drawings

PROCESS FOR THE PREPARATION OF ALKYLATED CYCLOPENTENONES

BRIEF SUMMARY OF THE INVENTION

The instant invention provides a process for the preparation of a cyclopentenone of formula

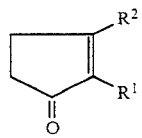
(I)

wherein each of symbols $R^1$ and $R^2$, when taken separately, represents an alkyl radical of $C_1$ to $C_6$, or a hydrogen atom, or, when taken together, they represent a polymethylene, or one of them designates a hydrogen atom and the other an alkyl radical of $C_1$ to $C_6$, which process consists in the catalytic cyclization of an ester having formula

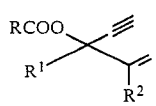
(II)

wherein $R^1$ and $R^2$ are defined as above and R stands for a $C_1$ to $C_6$ alkyl radical or a phenyl group, in the presence of a metallo-organic compound of formula $$MeX_2(R^3CN)_2 \quad (III)$$

wherein Me represents palladium or platinum, $R^3$ represents a $C_1$ to $C_3$ alkyl radical or a phenyl group and X defines a halogen atom, at a temperature of between about 50° and 100° C., and in isolating the desired cyclopentenone from the reaction mixture.

This invention further relates to some of the acetylenic esters having formula (II), viz.
1-ethynyl-2-pentyl-2-propenyl acetate,
1-ethynyl-2-hexyl-2-propenyl acetate,
1-ethynyl-2-methylene-cyclododecyl acetate and
1-ethynyl-1-pentyl-2-propenyl acetate.

BACKGROUND OF THE INVENTION

Certain cyclopentenones possessing an endocyclic double bond in the five membered ring and an alkyl substituent in the α- or β-position with respect to the carbonyl group represent useful raw materials for the synthesis of a variety of products destined to the perfumery and flavour industry, as well as to the pharmaceutical one, namely for the preparation of steroids.

Very numerous processes for their preparation have been described so far. For instance a review for the preparation of 2-methyl-2-cyclopentenone has been recently published by R. L. Funk and K. P. C. Vollhardt [see Synthesis 1980, 118].

For the preparation of other 2-cyclopentenones see also the references cited by F. Naef et al. [Helv. Chim. Acta, 61, 2524 (1978)], T. L. Ho et al. [Chem. Ind. (London) 1982, 371–372] and McCurry et al. [J. Org. Chem. 29, 2317–2319 (1974)].

The known methods are based on multistep uneconomical processes and their industrial exploitation suffer from this major drawback.

The instant invention, which is based on a new straightforward reaction, offers an original solution to this problem, thus enabling the industrial convenient preparation of these useful materials.

PREFERRED EMBODIMENTS OF THE INVENTION

The course of the reaction on which the present invention process is based is surprising as it is known in the art that allyl acetates, in the presence of palladium catalysts analogous to those of formula (III), undergo the following type of rearrangement:

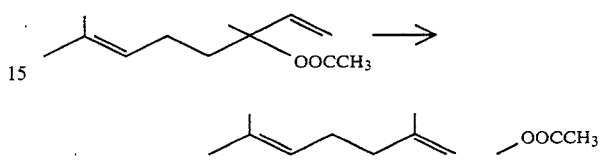

[see for instance:
(a) P. M. Henry, J. Am. Chem. Soc. 94, 5200 (1972);
(b) L. E. Overman & F. M. Knoll, Tetrahedron Lett. 1979, 321;
(c) P. A. Grieco, T. Takigawa, S. L. Bongers & H. Tanaka, J. Am. Chem. Soc. 102, 7587 (1980);
(d) P. A. Grieco, P. A. Tuthill & H. L. Sham, J. Org. Chem. 46, 5005 (1981);
(e) B. T. Golding, C. Pierpoint & R. Aneja, J. Chem. Soc. Chem. Comm. 1981, 1030].

The reaction can be effected in an organic solvent or in the absence of any solvent. On the other hand, traces of water do not seem to exert an influence on the good course of the reaction. Solvents include ethers such as tetrahydrofuran, nitriles, such as acetonitrile, halogenated hydrocarbons such as chloroform, or alcohols, especially tert-butanol or isopropanol. Acetonitrile is preferred.

The reaction can also be effected in the presence of a carboxylic acid. Suitable carboxylic acids include acetic, propionic or butyric acid. For carrying out the cyclization of esters (II) wherein $R=CH_3$, acetic acid is preferred.

As indicated above, the cyclization of esters (II) occurs in the presence of catalytic amounts of halogenated metallo-organic derivatives of palladium or platinum (III). Preferred are the chloro- and bromo-derivatives (X=Cl or Br).

As a ligand of platinum or palladium halide, it is preferred to use nitriles such as acetonitrile or benzonitrile; thus the reaction shall occur in the presence of $MeX_2(CH_3CN)_2$ or $MeX_2(C_6H_5CN)_2$ ]Me=Pt or Pd; X=halogen].

The proportion of the palladium or the platinum salts in the reaction mixture is of the order of about 5 to 10 moles % with respect to the molar quantity of the starting ester having formula (II).

The reaction times are relatively short and are of course a function of the temperature applied. We could observe that generally times of about 1–1 h 30 are sufficient to promote the reaction and drive it to completion.

Typically, a preferred mode of operation consists in bringing the mixture of ester (II) and palladium or platinum salt (III) in a molar ratio of about 20:1, to the chosen reaction temperature. After one hour, the reaction is stopped and the obtained mixture is distilled under reduced pressure to give the desired cyclopentenone (I).

The acetylenic esters of formula (II), used as starting materials in the above described process, can be easily obtained by esterification of the corresponding alcohols of which the one wherein $R^1=CH_3$ is commercially available. The others can be synthetically produced.

The reaction pathways given hereinbelow illustrate two of the methods which can be applied to this effect.

Pathway 1

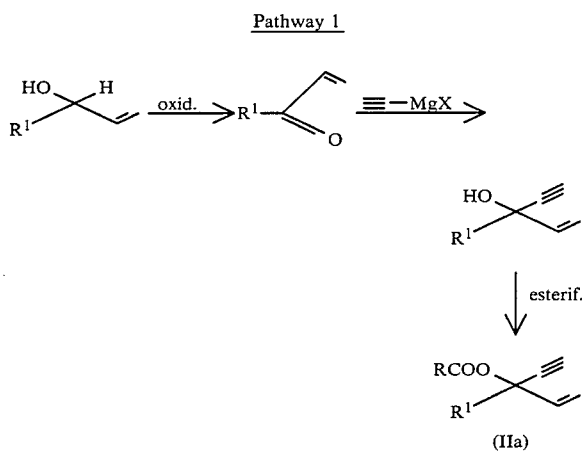

[see for example: Org. Synth. Coll. Vol. 4, 792 (1963) and Synthesis 1976, 755].

Pathway 2

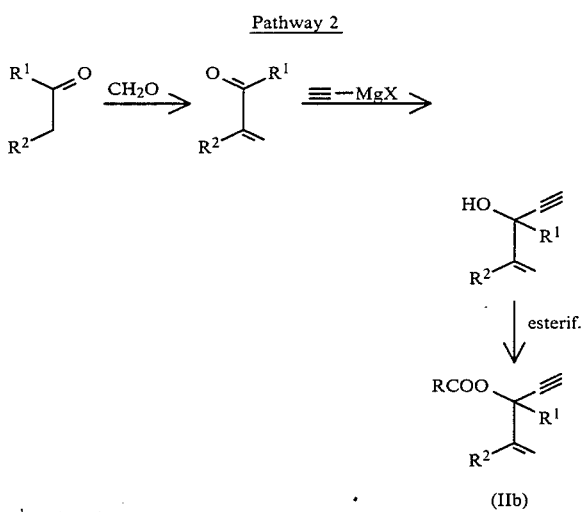

$R^1$ = H or alkyl

The invention is illustrated by but not limited to the following examples wherein the temperatures are indicated in degrees centigrade and the abbreviations have the meaning common in the art.

EXAMPLE 1

2-Methyl-2-cyclopentenone

A mixture of 250 mg (1.81 mM) of 1-ethynyl-1-methyl-2-propenyl acetate and 46 mg of $PdCl_2(CH_3CN)_2$ (0.18 mM) in 2.1 ml of acetonitrile and 100 μl of glacial acetic acid was heated at 60° during 45 minutes. A control via vpc indicated complete conversion of starting acetate. 1 Ml of methanol and 1 crystal of 4-dimethylaminopyridine were then added to the reaction mixture and the whole was stirred during 30 minutes at room temperature, whereupon 10 ml of 1:1 mixture of pentane/ether were added followed by a small quantity of potassium carbonate. Stirring was maintained for an additional hour and the mixture was filtered. The residue obtained by evaporation of the volatiles, was distilled in a bulb to bulb apparatus to give 101 mg of the desired cyclopentenone (purity 96%; yield 56%).

EXAMPLE 2

2-Pentyl-2-cyclopentenone

A mixture of 184 mg (0.95 mM) of 1-ethynyl-1-pentyl-2-propenyl acetate and 13 mg (0.05 mM) of $PdCl_2(CH_3CN)_2$ in 1.2 ml of acetonitrile and 60 μl of glacial acetic acid was heated at 80° during 2 h. 1 Ml of methanol and some crystals of 4-dimethylaminopyridine were added to the reaction mixture and the whole was stirred for 45 minutes at room temperature, whereupon 10 ml of a 1:1 mixture of pentane/ether were added followed by a small quantity of potassium carbonate. The reaction mixture was then stirred for 30 minutes, it was then filtered and evaporated. The obtained residue gave by bulb to bulb distillation 104 mg of a colorless distillate constituted by the desired product having a purity of 92% (yield 66%). By carrying out the reaction in toluene instead of acetonitrile at a temperature of about 80°, the desired product was obtained, though in lower yields.

1-Ethynyl-1-pentyl-2-propenyl acetate, used as starting material in the above described process was obtained according to a process similar to that previously described in Synthesis, 1976, 755. The analytical data of the obtained ester were the following:

NMR (360 MHz): 0.89 (3H, t, J=7); 1.23–1.60 (6H, m); 1.74–1.84; 1.92–2.00 (1H, m); 2.05 (3H, s); 2.68 (1H, s); 5.28 (1H, d, J=10.5); 5.58 (1H, d, J=17); 5.88 (1H, dxd, J=10.5 and 17) δ ppm;

MS: $M^+$ =194; m/z: 123(21), 96 (13), 95 (11), 81 (21), 78 (11), 43 (100);

IR: 1750, 2140, 3290 $cm^{-1}$.

By following the same process as that described above in Examples 1 and 2, the following cyclopentenones were prepared:

| product | yield (%) |
| --- | --- |
| 3-pentyl-2-cyclopentenone | 66 |
| 3-hexyl-2-cyclopentenone | 63 |
| 13-oxo-bicyclo[10.3.0]pentadec-1(12)-ene | 76–89 |

The starting acetylenic acetates presented the following analytical characteristics:

1-ethynyl-2-pentyl-2-propenyl acetate

NMR (360 MHz): 0.90 (3H, t, J=7.0; 1.25–1.37 (4H, m); 1.45–1.58 (2H, m), 2.12 (3H, s); 2.09–2.23 (2H, m); 2.54 (1H, d, J=2.2); 5.05, 5.34, 5.85 (3x1H, broad s) δ ppm;

MS: $M^+$ =194 (<0.1); m/z: 105 (33), 95 (27), 91 (52), 79 (26), 77 (28), 43 (100), 41 (36).

1-ethynyl-2-hexyl-2-propenyl acetate

NMR (360 MHz): 0.90 (3H, t, J=7.5); 1.25–1.39 (6H, m), 1.44–1.56 (2H, m); 2.12 (3H, s); 2.09–2.23 (2H, m); 2.45 (1H, d, J=1.8); 5.05, 5.34, 5.85 (3x1H, broad s) δ ppm;

MS: $M^+$ =208 (<0.1); m/z: 105 (24), 95 (16), 91 (43), 79 (20), 77 (18), 43 (100), 41 (34).

1-ethynyl-2-methylene-cyclododecyl acetate

NMR (360 MHz): 1.16–1.60 (14H, m); 1.76–2.04 (4H, m); 2.06 (3H, s); 2.14–2.26 (2H, m); 2.72 (1H, s); 5.16 (1H, broad s); 5.63 (1H, d, J=2.2) δ ppm;

MS: M$^+$=262 (<0.1); m/z: 95 (22), 91 (28), 79 (19), 67 (19), 55 (26), 43 (100), 41 (30), IR: 2110, 1740 cm$^{-1}$.

m.p. 66°–68°.

What I claim is:

1. A process for the preparation of a cyclopentenone having formula

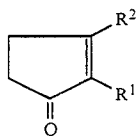 (I)

wherein each of symbols $R^1$ and $R^2$, when taken separately, represents an alkyl radical of $C_1$ to $C_6$, or a hydrogen atom, or, when taken together, they represent a polymethylene, or one of them designates a hydrogen atom and the other an alkyl radical of $C_1$ to $C_6$, which consists in the catalytic cyclization of an ester having formula

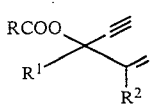 (II)

wherein $R^1$ and $R^2$ are defined as above and R stands for a $C_1$ to $C_6$ alkyl radical or a phenyl group, in the presence of a metallo-organic compound of formula $$MeX_2(R^3CN)_2 \quad (III)$$

wherein Me represents palladium or platinum, $R^3$ represents a $C_1$ to $C_3$ alkyl radical or a phenyl group and X defines a halogen atom, at a temperature of between about 50° and 100° C., and in isolating the desired cyclopentenone from the reaction mixture.

2. A process according to claim 1, wherein the reaction is carried out in the presence of an organic solvent.

3. A process according to claim 1, wherein the organic solvent is acetonitrile or acetic acid, or any mixture thereof.

4. A process according to claim 1, wherein the compound of formula (II) is 1-ethynyl-1-methyl-2-propenyl acetate and the obtained cyclopentenone is 2-methyl-2-cyclopentenone.

5. A process according to claim 1, wherein the compound of formula (II) is 1-ethynyl-1-pentyl-2-propenyl acetate and the obtained cyclopentenone is 2-pentyl-2-cyclopentenone.

6. A process according to claim 1, wherein the compound of formula (II) is 1-ethynyl-2-pentyl-2-propenyl acetate and the obtained cyclopentenone is 3-pentyl-2-cyclopentenone.

7. A process according to claim 1, wherein the compound of formula (II) is 1-ethynyl-2-hexyl-2-propenyl acetate and the obtained cyclopentenone is 3-hexyl-2-cyclopentenone.

8. A process according to claim 1, wherein the compound of formula (II) is 1-ethynyl-2-methylene-cyclododecyl acetate and the obtained cyclopentenone is 13-oxo-bicyclo[10.3.0]pentadec-1(12)-ene.

9. 1-Ethynyl-2-pentyl-2-propenyl acetate.

10. 1-Ethynyl-2-hexyl-2-propenyl acetate.

11. 1-Ethynyl-2-methylene-cyclododecyl acetate.

12. 1-Ethynyl-1-pentyl-2-propenyl acetate.

* * * * *